United States Patent [19]

Schulze et al.

[11] Patent Number: 5,051,370
[45] Date of Patent: Sep. 24, 1991

[54] METHOD FOR THE EVALUATION OF AGGLUTINATION REACTIONS

[75] Inventors: Detlef Schulze, Frankfurt am Main; Rudolf Schmidtberger, Marburg, both of Fed. Rep. of Germany

[73] Assignee: Hoechst Aktiengesellschaft, Frankfurt am Main, Fed. Rep. of Germany

[21] Appl. No.: 536,501

[22] Filed: Jun. 11, 1990

[30] Foreign Application Priority Data

Jun. 13, 1989 [DE] Fed. Rep. of Germany ....... 3919260

[51] Int. Cl.$^5$ .................. G01N 21/03; G01N 33/543; G01N 33/00
[52] U.S. Cl. .................... 436/165; 436/518; 436/805; 422/73
[58] Field of Search ............... 422/63, 65, 73; 436/43, 436/46, 47, 50, 69, 164, 165, 171, 517, 803, 807, 808, 824; 356/426, 427, 428

[56] References Cited

U.S. PATENT DOCUMENTS 3,997,272  12/1976  George .................................. 356/427
4,400,353  8/1983  Meserol et al. ...................... 356/338

Primary Examiner—David L. Lacey
Assistant Examiner—Thomas E. Daley
Attorney, Agent, or Firm—Finnegan, Henderson, Farabow, Garrett, and Dunner

[57] ABSTRACT

In the method for the evaluation of agglutination reactions between a reagent and a biological fluid to be examined, the reagent and the biological fluid are intimately mixed by agitation with a tumbling motion. The mixture is then placed in the ray path of an optical measuring system and, while maintaining the tumbling motion and superimposing a translational motion at right angles to the optical axis of the measuring system, an image of the agglutinates formed in the mixture is produced on a focusing screen, and the image is evaluated with an evaluation unit.

4 Claims, 2 Drawing Sheets

METHOD FOR THE EVALUATION OF AGGLUTINATION REACTIONS

The invention relates to a method for the quantitative evaluation of agglutination reactions between a reagent and a biological fluid.

Agglutination reactions serve as a diagnostic method for the discovery and identification of certain diseases such as myocardial infarcts, inflammations, rheumatoid factors etc. In the test required for the diagnosis, biological fluid, such as blood serum, is mixed with a specific antigen on a blackened test plate and left to react for about 2 minutes with a tumbling motion. If antibodies which react with the specific antigen are present in the serum, there is formation of agglutinates which can be visually identified depending on the concentration of the antibodies in the serum. If agglutinates are identified even before the 2 minutes have elapsed, it is also possible to draw rough conclusions about the concentration thereof if appropriate serial dilutions are employed for assessing the agglutination reactions. As a rule, control measurements with positive and negative sera are necessary in these tests. In all cases, the quality of the assessment depends on the experience of the observer. The intention of the invention is to provide a remedy for this.

The object is achieved by a method of the type specified in the introduction, which comprises intimately mixing the reagent and the biological fluid by agitation with a tumbling motion, then placing the mixture in the ray path of an optical measuring system and, while maintaining the tumbling motion and superimposing a translational motion at right angles to the optical axis of the measuring system, producing on a focusing screen an image of the agglutinates formed in the mixture, and evaluating the image with an evaluation unit.

It is possible with this method to determine accurately and reproducibly the time at which an agglutination reaction occurs. The method furthermore makes it possible to evaluate concentration-dependent kinetics, and it is possible, by means of a recorded calibration plot, to determine the concentration of the agglutinates from the measured signals from an unknown reaction.

The method is explained more detail hereinafter by means of the drawings.

Figure 1:
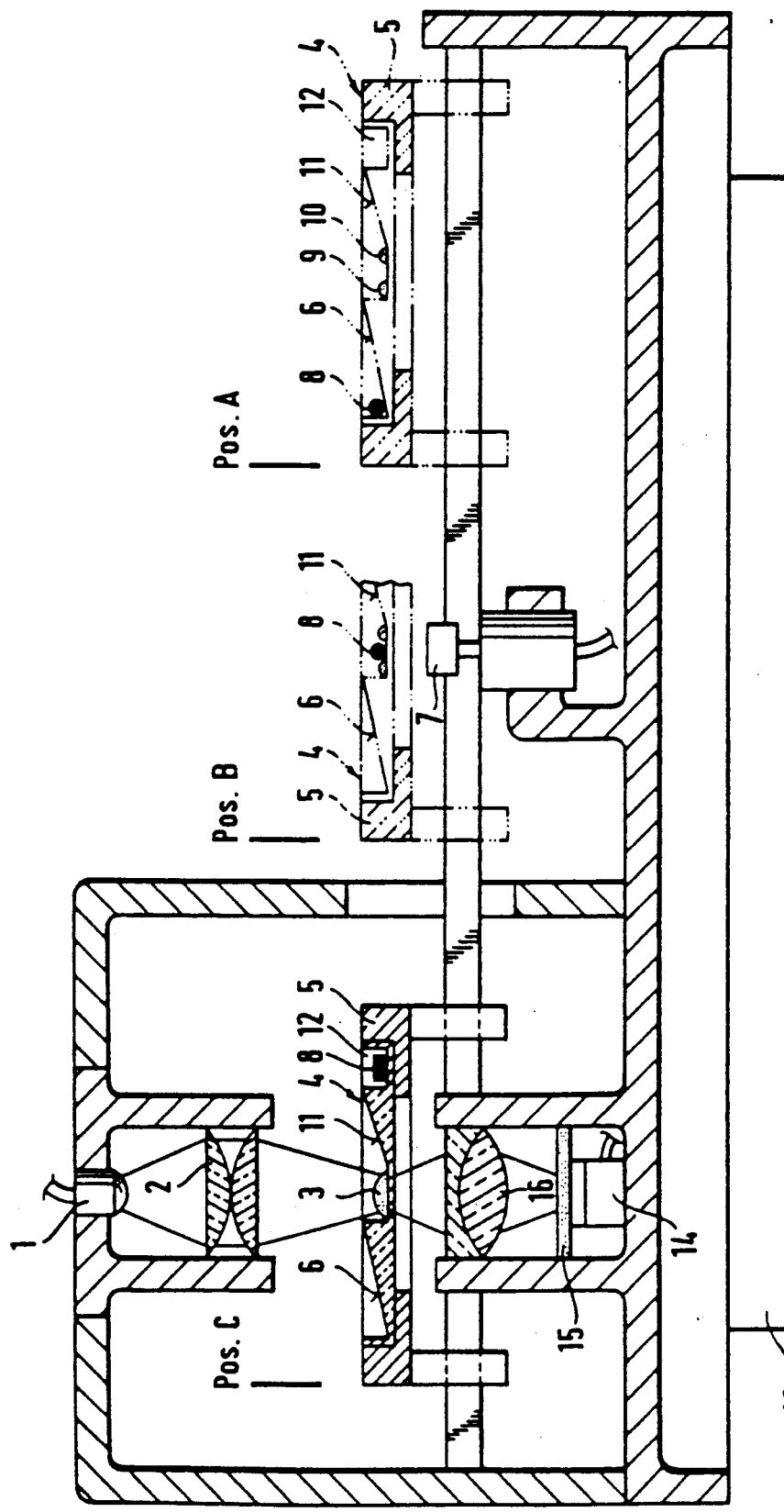
FIG. 1 shows the measuring system in a section from the side.
Figure 2A:
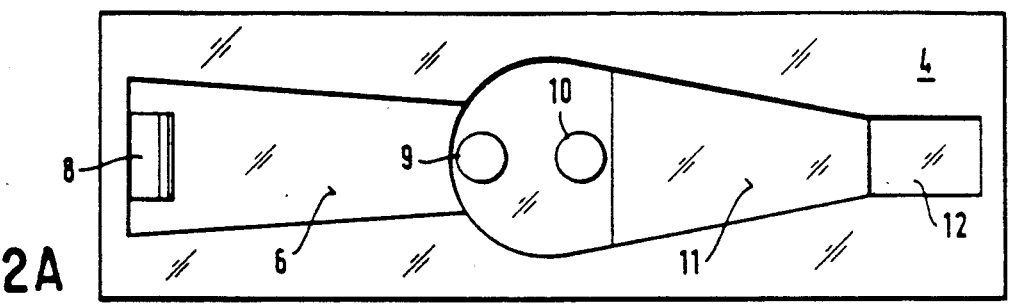
FIG. 2 shows the slide from above in each of positions A, B and C.
Figure 2B:
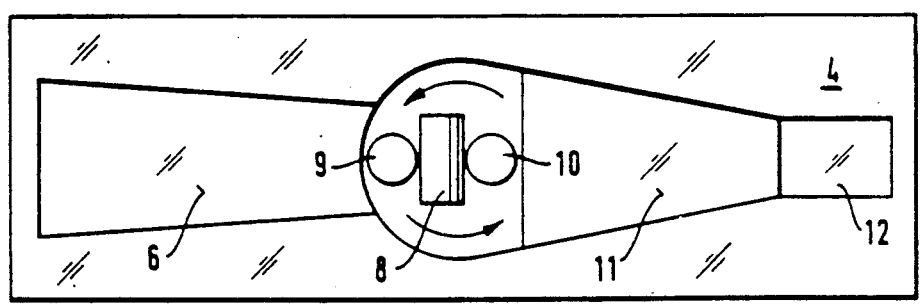
Figure 2C:
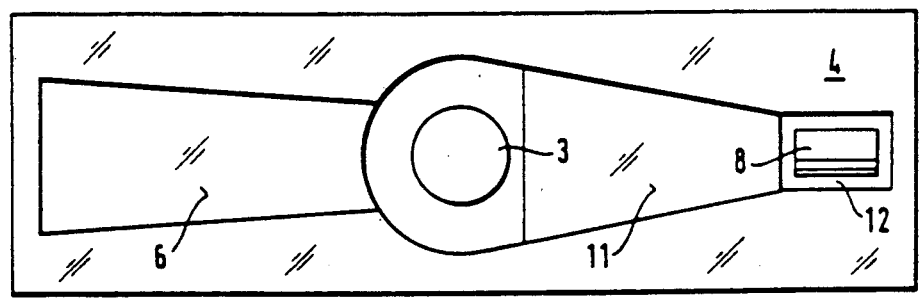
Figure 3:
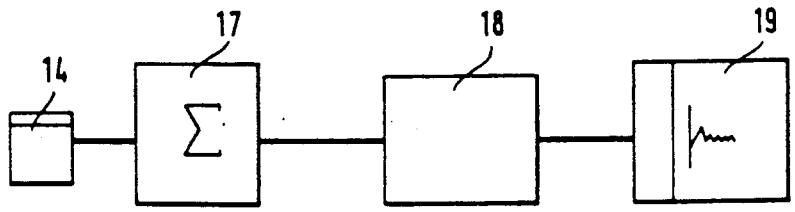
FIG. 3 shows the evaluation device diagrammatically.

A reagent 9 and a biological fluid to be examined, for example a patient's serum 10, are pipetted onto a slide 4 which is located in position A on a carriage 5. After the pipetting process, the carriage travels, driven by a motor or manually (not depicted), into position B. At the same time, a ferromagnetic stirring bar 8 of a magnetic stirrer 7 is drawn over an incline 6 into a well in which are located the reagent 9 and the serum 10. The magnetic stirrer 7 begins to rotate and thereby moves the stirring bar 8 which mixes the reagent 9 and the serum 10. A time measurement takes place, with the aid of a computer 18 which is part of an evaluation unit (FIG. 3), with the start of the stirring process. At the same time, the entire measuring system is set in a tumbling motion by a tumbler 13. The tumbling motion is a rotating motion on which is superimposed a tilting motion. This form of motion ensures uniform motion of the reagent in the fluid drop 3 to be examined. If antibodies are present in the serum, the agglutinates which can be observed distinctly with a microscope are produced after a measurable reaction time. After a few seconds the magnetic stirrer 7 is switched off and the carriage 5 travels into position C under an optical measuring system consisting of light source 1, condenser 2, objective 16 and focusing screen 15. During the movement to position C, the stirring bar 8 is drawn over another incline 11 into a depression 12 and immobilized there. In position C, the carriage 5 is subjected to a translational motion at right angles to the optical axis of the measuring system with a frequency of 0.5 to 5 Hz, preferably with 1 Hz. The translational motion is superimposed on the tumbling motion. The fluid drop 3 on the slide 4 is illuminated by a light source 1 and, because of the simultaneous translational motion of the carriage 5, sharp images are produced of the agglutinates which are forming from a narrow strip of the drop 3 by the objective 16 on the focusing screen 15. The agglutinate images are detected with a detector 14 and converted into electrical impulses which are counted with a counter 17. After a certain time, the agglutination time, the number of measured signals increases greatly. This time is recorded and displayed. Connection of a plotter 19 allows the course of measurement to be depicted graphically. This entails the impulses being plotted against time. The concentration of the agglutinates is determined by comparing the measured signals of the serum to be evaluated in a calibration plot.

We claim:

1. A method for the evaluation of agglutination reactions between a reagent and a biological fluid, comprising
   mixing the reagent and the biological fluid by agitation employing a tumbling motion;
   placing the mixture in the ray path of an optical measuring system;
   superimposing a translational motion at right angles to the optical axis of the measuring system while maintaining said tumbling motion;
   producing on a focusing screen an image of any agglutinates formed in the mixture; and
   evaluating the image with an evaluation unit.

2. A method according to claim 1, wherein said evaluation is a qualitative evaluation of said agglutination reactions between said reagent and said biological fluid.

3. A method according to claim 1, wherein said evaluation is a quantitative evaluation of said agglutination reactions between said reagent and said biological fluid.

4. A method according to claim 3, wherein said quantitative evaluation is the determination of the concentration of the agglutinates formed and said quantitative evaluation employs a calibration plot.

* * * * *